United States Patent [19]

Becker et al.

[11] Patent Number: 5,207,816
[45] Date of Patent: * May 4, 1993

[54] CYCLOHEXENONE DERIVATIVES AND THEIR USE FOR CONTROLLING UNDESIRABLE PLANT GROWTH

[75] Inventors: Rainer Becker, Bad Duerkheim; Dieter Jahn, Edingen-Neckarhausen; Michael Keil, Freinsheim; Hans Theobald, Limburgerhof; Wolfgang Spiegler, Worms; Bruno Wuerzer, Otterstadt, all of Fed. Rep. of Germany

[73] Assignee: BASF Aktiengesellschaft, Ludwigshafen, Fed. Rep. of Germany

[*] Notice: The portion of the term of this patent subsequent to Nov. 14, 2006 has been disclaimed.

[21] Appl. No.: 711,392

[22] Filed: Jun. 6, 1991

Related U.S. Application Data

[63] Continuation of Ser. No. 552,853, Jul. 12, 1990, abandoned, which is a continuation of Ser. No. 370,068, Jun. 22, 1989, abandoned, which is a continuation of Ser. No. 149,937, Jan. 28, 1988. abandoned, which is a continuation of Ser. No. 717,009. Mar. 28, 1985, abandoned.

[30] Foreign Application Priority Data

Mar. 29, 1984 [DE] Fed. Rep. of Germany ....... 3430229
Aug. 17, 1984 [DE] Fed. Rep. of Germany ....... 3411530

[51] Int. Cl.$^5$ .................. A01N 43/24; C07D 261/06; C07D 261/08; C07D 261/12
[52] U.S. Cl. .................................... 504/271; 504/273; 504/280; 504/289; 504/294; 504/299; 504/283; 504/275; 504/266; 504/272; 504/265; 504/269; 504/263; 504/277; 504/270; 504/261; 548/243; 548/244; 548/245; 548/246; 548/247; 548/206; 548/213; 548/214; 548/136; 548/143; 548/144; 548/131; 548/132; 548/133; 548/205; 548/255; 548/267.4; 548/377.1; 548/343.5; 548/345.1; 548/316.4; 548/373.1; 548/561; 549/77; 549/496; 549/479
[58] Field of Search ............................ 71/88; 548/247

[56] References Cited

U.S. PATENT DOCUMENTS

| | | | |
|---|---|---|---|
| 4,422,864 | 12/1983 | Becker et al. | 71/88 |
| 4,602,935 | 7/1986 | Becker et al. | 71/88 |
| 4,604,132 | 8/1986 | Conway et al. | 548/202 |
| 4,704,157 | 11/1987 | Conway et al. | 71/90 |
| 4,715,884 | 12/1987 | Watson et al. | 71/90 |
| 4,761,486 | 11/1989 | Kolassa et al. | 71/88 |
| 5,034,047 | 7/1991 | Kolassa et al. | 548/247 |

FOREIGN PATENT DOCUMENTS 1202634 4/1986 Canada .
0125094 11/1984 European Pat. Off. .
1461170 1/1977 United Kingdom .

OTHER PUBLICATIONS

Chemical Abstracts, vol. 91, 608 (1979)-Japanese Preliminary Published Application No. 63,052.
Tetrahedron Letters, 29, 2491 (1975).

Primary Examiner—Cecilia Tsang
Assistant Examiner—E. Bernhardt
Attorney, Agent, or Firm—Keil & Weinkauf

[57] ABSTRACT

Cyclohexenone derivatives of the formula

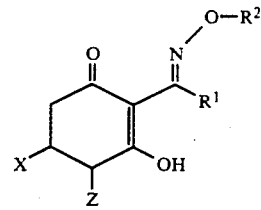

where $R^1$ is alkyl, $R^2$ is alkyl, unsubstituted or halogen-substituted alkenyl or alkynyl, X is a substituted or unsubstituted five-membered heteroaromatic radical, and Z is hydrogen, methoxycarbonyl, ethoxycarbonyl, methyl or cyano, processes for their manufacture, and the use of these compounds for controlling undesirable plant growth.

12 Claims, No Drawings

CYCLOHEXENONE DERIVATIVES AND THEIR USE FOR CONTROLLING UNDESIRABLE PLANT GROWTH

This is a continuation of Ser. No. 07/552,853, filed Jul. 12, 1990; which is a continuation of Ser. No. 07/149,937, filed Jan. 28, 1988; which is a continuation of Ser. No. 07/370,068, filed Jun. 22, 1989; which is continuation of Ser. No. 06/717,009, filed Mar. 28, 1985 all now abandoned.

The present invention relates to cyclohexenone derivatives and to herbicides which contain these compounds as active ingredients.

It has been disclosed that cyclohexenone derivatives can be used for controlling undesirable grasses in broad-leaved crops (German Laid-Open Applications DOS 2,439,104 and DOS 3,123,312).

We have found that cyclohexenone derivatives of the formula

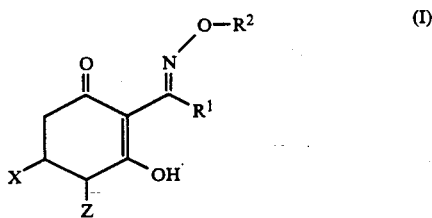

where $R^1$ is alkyl of 1 to 4 carbon atoms, $R^2$ is alkyl of 1 to 4 carbon atoms, unsubstituted or halogen-substituted alkenyl of 3 to 5 carbon atoms or alkynyl of 3 to 5 carbon atoms, X is an unsubstituted or substituted five-membered heteroaromatic radical having 1 to 3 heteroatoms selected from the group consisting of oxygen, nitrogen and sulfur, with the exception of unsubstituted fur-2-yl, unsubstituted thien-2-yl, unsubstituted pyrrolyl, methyl-substituted pyrrolyl and pyrazolyl, and Z is hydrogen, methoxycarbonyl, ethoxycarbonyl, methyl or cyano, and salts of these compounds possess herbicidal activity.

The compounds of the formula I can occur in tautomeric forms, all of which are embraced by the claims:

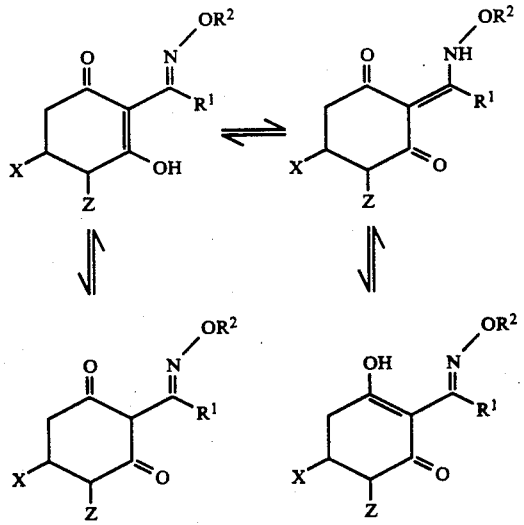

In formula I, for example, $R^1$ is straight-chain or branched alkyl of 1 to 4 carbon atoms, i.e. methyl, ethyl, n-propyl, isopropyl, n-butyl, sec.-butyl, isobutyl or tert.-butyl; $R^2$ is straight-chain or branched alkyl of 1 to 4 carbon atoms, unsubstituted or halogen-substituted alkenyl of 3 to 5 carbon atoms, halogen being, in particular, bromine or chlorine, or alkynyl of 3 to 5 carbon atoms, such as methyl, ethyl, n-propyl, isopropyl, n-butyl, sec.-butyl, isobutyl, tert.-butyl, allyl, 1-chloroprop-1-en-3-yl, 2-chloroprop-1-en-3-yl, 1,2-dichloroprop-1-en-3-yl, 1,2-dibromoprop-1-en-3-yl, 1,1,2-trichloroprop-1-en-3-yl or propargyl; Z is hydrogen, methoxycarbonyl, ethoxycarbonyl, methyl or cyano; and X is a five-membered heteroaromatic radical having 1 to 3 heteroatoms, which may be oxygen, nitrogen or sulfur, such as imidazolyl, 1,2,3-triazolyl, 1,2,4-triazolyl, isoxazolyl, isothiazolyl, oxazolyl, thiazolyl, 1,2,4-oxadiazolyl, 1,3,4-oxadiazolyl, 1,3,4-thiadiazolyl, thien-3-yl, fur-3-yl, substituted (with the exception of methylated) pyrrolyl and pyrazolyl, e.g. imidazol-2-yl, imidazol-4-yl, 1,2,3-triazol-4-yl, 1,2,4-triazol-3-yl, isoxazol-3-yl, isoxazol-4-yl, isoxazol-5-yl, isothiazol-3-yl, isothiazol-4-yl, isothiazol-5-yl, oxazol-2-yl, oxazol-4-yl, oxazol-5-yl, thiazol-2-yl, thiazol-4-yl, thiazol-5-yl, 1,2,4-oxadiazol-5-yl, 1,2,4-oxadiazol-3-yl, 1,3,4-oxadiazol-2-yl or 1,3,4-thiadiazol-2-yl, and these radicals can be substituted by phenyl, phenoxy, phenyl which is substituted by halogen, $C_1$–$C_4$-alkyl or $C_1$–$C_4$-haloalkyl, in particular chlorine, bromine, fluorine, methyl, ethyl, trifluoromethyl or difluoromethyl, such as 4-chlorophenyl, 3,4-dichlorophenyl, 3-trifluoromethylphenyl or 4-methylphenyl, phenoxy which is substituted by halogen, $C_1$–$C_4$-alkyl or $C_1$–$C_4$-haloalkyl, in particular chlorine, bromine, fluorine, methyl, ethyl, trifluoromethyl or difluoromethyl, halogen, such as fluorine, chlorine, bromine or iodine, alkyl of 1 to 4 carbon atoms, such as methyl, ethyl, isopropyl or tert.-butyl, cycloalkyl of 3 to 7 carbon atoms, such as cyclohexyl, dialkylamino where alkyl is of 1 to 4 carbon atoms, such as dimethylamino, diethylamino or di-n-butylamino, or alkoxy of 1 to 4 carbon atoms, such as methoxy, ethoxy, isopropoxy, n-butoxy, sec.-butoxy or tert.-butoxy, and X may furthermore be a fur-2-yl radical which is substituted by the abovementioned radicals.

Examples of agriculturally suitable salts of the compounds of the formula I are the alkali metal salts, such as potassium salts or sodium salts, alkaline earth metal salts, such as calcium salts, barium salts or magnesium salts, manganese, copper, zinc and iron salts, and ammonium and phosphonium salts.

Preferred compounds of the formula I carry, as substituent X, an imidazolyl, 1,2,3-triazolyl, 1,2,4-triazolyl, isoxazolyl, isothiazolyl, thien-3-yl, fur-3-yl, substituted (but not methylated) pyrrolyl or pyrazolyl radicals e.g. imidazol-2-yl, imidazol-4-yl, 1,2,3-triazol-4-yl, 1,2,4-triazol-3-yl, isoxazol-3-yl, isoxazol-4-yl, isoxazol-5-yl, isothiazol-3-yl, isothiazol-4-yl or isothiazol-5-yl, and these radicals can be substituted by phenyl, phenoxy, phenyl which is substituted by halogen, $C_1$–$C_4$-alkyl or $C_1$–$C_4$-haloalkyl, in particular chlorine, bromine, fluorine, methyl, ethyl, trifluoromethyl or difluoromethyl, such as 4-chlorophenyl, 3,4-dichlorophenyl, 3-trifluoromethylphenyl or 4-methylphenyl, phenoxy which is substituted by halogen, $C_1$–$C_4$-alkyl or $C_1$–$C_4$-haloalkyl, in particular chlorine, bromine, fluorine, methyl, ethyl, trifluoromethyl or difluoromethyl, halogen, such as fluorine, chlorine, bromine or iodine, alkyl of 1 to 4 carbon atoms, such as methyl, ethyl, isopropyl or tert.-butyl, cycloalkyl of 3 to 7 carbon atoms, such as cyclohexyl, dialkylamino where alkyl is of 1 to 4 carbon atoms, such as dimethylamino, diethylamino, di-s-butylamino or di-n-butylamino, or alkoxy of 1 to 4 carbon atoms, such as methoxy, ethoxy, isopropoxy, n-butoxy, sec.-butoxy or tert.-butoxy. X is particularly preferably unsubstituted or substituted isoxazolyl.

Other preferred cyclohexenone derivatives of the formula I are those in which Z is hydrogen.

The compounds of the formula I can be obtained by, for example, reacting a compound of the formula

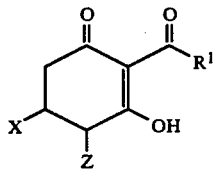

(II)

where $R^1$, X and Z have the above meanings, with a hydroxylamine derivative $R^2O$-$NH_3Y$, where $R^2$ has the above meanings and Y is any anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. It is also possible to use organic bases, such as pyridine or tertiary amines.

The reaction proceeds particularly readily at a pH of from 2 to 9, in particular from 4.5 to 5.5, the pH advantageously being established by adding an acetate, for example an alkali metal acetate, in particular sodium acetate or potassium acetate, or a mixture of the two salts. Alkali metal acetates are added in amounts of, for example, from 0.5 to 2 moles, based on the ammonium compound of the formula $R^2O$—$NH_3Y$.

Examples of suitable solvents are dimethyl sulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water and extracting with a non-polar solvent, such as methylene chloride, and distilling off the solvent under reduced pressure.

The compound of the formula I can furthermore be obtained by reacting a compound of the formula II with a hydroxylamine of the formula $R^2O$—$NH_2$, where $R^2$ has the above meanings, in an inert diluent at from 0° C. to the boiling point of the reaction mixture, in particular from 15° to 70° C. If necessary, the hydroxylamine can be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The compounds of the formula I can furthermore be obtained by reacting a compound of the formula II with an unsubstituted hydroxylammonium salt $NH_2OH.HY$, in which Y has the above meaning, to give the corresponding oxime, and then O-alkylating the latter. In this procedure, the tendency of the oximes formed as intermediates to undergo undesirable cyclization reactions must be borne in mind; this tendency can be influenced by means of suitable assistants and reaction conditions.

Suitable solvents are those listed for the reaction of the compounds of the formula II with hydroxylamines, while suitable bases are the basic substances stated for the reaction of the compounds of the formula II with hydroxylamine derivatives of the formula $R^2$—O—$NH_3Y$, twice the amount of base being required.

The alkali metal salts of the compounds of the formula I can be obtained by treating these compounds with sodium hydroxide or potassium hydroxide in aqueous solution or in an organic solvent, such as methanol, ethanol or acetone. Sodium alcoholates and potassium alcoholates can also be used as bases.

The other metal salts, e.g. the manganese, copper, zinc, iron, calcium, magnesium and barium salts, can be prepared from the sodium salts by reaction with the corresponding metal chlorides in aqueous solution. Ammonium and phosphonium salts can be prepared by reacting compounds of the formula I with ammonium or phosphonium hydroxides, if necessary in aqueous solution.

The compounds of the formula II can be prepared by a conventional method (Tetrahedron Lett. 29 (1975) 2491) from cyclohexane-1,3-diones of the formula IV, which can also occur in the tautomeric forms Iva and Ivb:

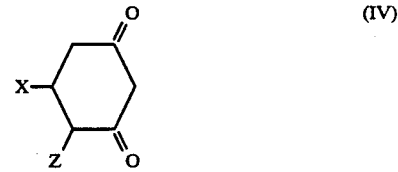

(IV)

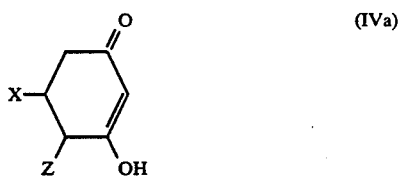

(IVa)

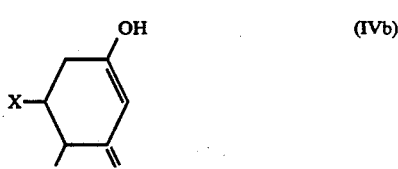

(IVb)

It is also possible to prepare compounds of the formula II via the enol-ester intermediates, which are obtained, possibly as isomer mixtures, in the conversion of compounds of the formula IV, and undergo a rearrangement reaction in the presence of imidazole derivatives or pyridine derivatives (Japanese Preliminary Published Application 79/063052).

The compounds of the formula IV are obtained by methods known from the literature, as shown in the equation below:

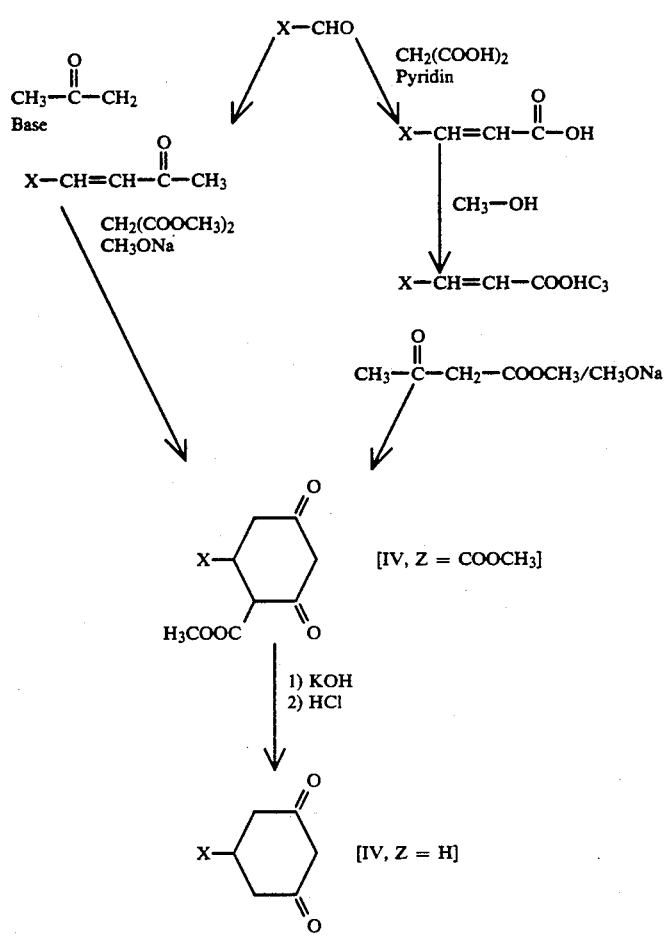

The method of introducing the substituent X may of course be altered from case to case and may differ from the above method; furthermore, a substituent X which has been introduced can be changed subsequently.

The Example which follows illustrates the preparation of the novel cyclohexenone derivatives of the formula I. Parts by weight bear the same relation to parts by volume as that of the kilogram to the liter.

EXAMPLE 9.9 parts by weight of 2-butyryl-5-(N-phenylpyrrol-3-yl)-cyclohexane-1,3-dione in 100 parts by volume of ethanol are taken, and 3.02 parts by weight of ethoxyammonium chloride and 2.79 parts by weight of sodium acetate are added. Stirring is carried out for several hours at room temperature, after which the mixture is poured into ice water and extracted with methylene chloride, and the extract is evaporated down. 11.0 parts by weight of 2-(1-ethoxyaminobutylidene)-5-(N-phenylpyrrol-3-yl)-cyclohexene-1,3-dione remain as a yellowish oil of refractive index $n^{23}=1.5894$ (compound No.1).

The compounds of the formula I below are prepared by a similar method. Compounds for which no characteristic data appear can be obtained by appropriately modifying the above method. Because of their structural similarity, they are expected to have a similar biological action.

| Compound no. | $R^1$ | $R^2$ | X | Z | M.p. [°C.]/$n_D$ |
|---|---|---|---|---|---|
| 1 | n-$C_3H_7$ | $C_2H_5$ | N-phenyl-pyrrol-3-yl | H | 1.5894 (23° C.) |
| 2 | n-$C_3H_7$ | $CH_2CH=CH_2$ | N-phenyl-pyrrol-3-yl | H | |
| 3 | n-$C_3H_7$ | $CH_2CH=CHCl$ | N-phenyl-pyrrol-3-yl | H | |
| 4 | n-$C_3H_7$ | $CH_2CCl=CH_2$ | N-phenyl-pyrrol-3-yl | H | |
| 5 | n-$C_3H_7$ | $C_2H_5$ | 2-phenyl-pyrazol-3-yl | $COOCH_3$ | |
| 6 | n-$C_3H_7$ | $C_2H_5$ | 2-phenyl-pyrazol-3-yl | H | viscous oil |
| 7 | n-$C_3H_7$ | $CH_2CH=CH_2$ | 2-phenyl-pyrazol-3-yl | H | viscous oil |
| 8 | n-$C_3H_7$ | $CH_2CH=CHCl$ | 2-phenyl-pyrazol-3-yl | H | |
| 9 | n-$C_3H_7$ | $CH_2CH=CH_2$ | 2-phenyl-thiazol-4-yl | $COOCH_3$ | |
| 10 | n-$C_3H_7$ | $C_2H_5$ | 2-phenyl-thiazol-4-yl | H | |
| 11 | n-$C_3H_7$ | $CH_2CH=CH_2$ | 2-phenyl-thiazol-4-yl | H | |
| 12 | n-$C_3H_7$ | $CH_2CCL=CH_2$ | 2-phenyl-thiazol-4-yl | H | |
| 13 | n-$C_3H_7$ | $CH_2CH=CHCl$ | 2-phenyl-thiazol-4-yl | H | |
| 14 | n-$C_3H_7$ | $C_2H_5$ | 5-phenoxy-furan-2-yl | $COOC_2H_5$ | |
| 15 | n-$C_3H_7$ | $C_2H_5$ | 5-phenoxy-furan-2-yl | H | 1.5508 (28° C.) |

-continued

| Compound no. | R¹ | R² | X | Z | M.p. [°C.]/$n_D$ |
|---|---|---|---|---|---|
| 16 | n-C₃H₇ | CH₂CH=CH₂ | 5-phenoxy-furan-2-yl | H | 1.5561 (28° C.) |
| 17 | n-C₃H₇ | CH₂CH=CH₂ | 5-(2-chlorophenoxy)-fur-2-yl | COOCH₃ | |
| 18 | n-C₃H₇ | C₂H₅ | 5-(2-chlorophenoxy)-fur-2-yl | H | 1.5602 (27° C.) |
| 19 | n-C₃H₇ | CH₂CH=CH₂ | 5-(2-chlorophenoxy)-fur-2-yl | H | 1.5608 (27° C.) |
| 20 | n-C₃H₇ | n-C₃H₇ | 5-(2-chlorophenoxy)-fur-2-yl | H | 1.5388 (27° C.) |
| 21 | C₂H₅ | n-C₃H₇ | 5-(2-chlorophenoxy)-fur-2-yl | H | 1.5605 (31° C.) |
| 22 | C₂H₅ | CH₂CH=CH₂ | 5-(2-chlorophenoxy)-fur-2-yl | H | 1.5685 (31° C.) |
| 23 | C₂H₅ | C₂H₅ | 2-(4-chlorophenyl)-thizol-4-yl | H | |
| 24 | C₂H₅ | CH₂CH=CH₂ | 2-(4-chlorophenyl)-thizol-4-yl | H | |
| 25 | n-C₃H₇ | C₂H₅ | 2-(4-chlorophenyl)-thizol-4-yl | COOC₂H₅ | |
| 26 | n-C₃H₇ | C₂H₅ | 2-(4-chlorophenyl)-thizol-4-yl | H | 98 |
| 27 | n-C₃H₇ | CH₂CH=CH₂ | 2-(4-chlorophenyl)-thizol-4-yl | H | 68 |
| 28 | n-C₃H₇ | CH₂CH=CHCl | 2-(4-chlorophenyl)-thizol-4-yl | H | |
| 29 | n-C₃H₇ | CH₂CCl=CH₂ | 2-(4-chlorophenyl)-thizol-4-yl | H | |
| 30 | n-C₃H₇ | C₂H₅ | 1-phenyl-pyrazol-4-yl | H | 57–60 |
| 31 | n-C₃H₇ | CH₂CH=CH₂ | 1-phenyl-pyrazol-4-yl | H | 59–60 |
| 32 | n-C₃H₇ | n-C₃H₇ | 1-phenyl-pyrazol-4-yl | H | |
| 33 | n-C₃H₇ | CH₂CH=CHCl | 1-phenyl-pyrazol-4-yl | H | 80 |
| 34 | n-C₃H₇ | propargyl | 1-phenyl-pyrazol-4-yl | H | 62 |
| 35 | n-C₃H₇ | C₂H₅ | 2-dimethylamino-oxazol-5-yl | H | |
| 36 | n-C₃H₇ | CH₂CH=CH₂ | 2-dimethylamino-oxazol-5-yl | H | |
| 37 | n-C₃H₇ | C₂H₅ | 3-methyl-1,2,4-oxadiazol-5-yl | H | |
| 38 | n-C₃H₇ | CH₂CH=CH₂ | 3-methyl-1,2,4-oxadiazol-5-yl | H | |
| 39 | n-C₃H₇ | C₂H₅ | 2-methyl-thiazol-4-yl | H | |
| 40 | n-C₃H₇ | CH₂CH=CH₂ | 2-methyl-thiazol-4-yl | H | |
| 41 | n-C₃H₇ | CH₂CH=CHCl | 2-methyl-thiazol-4-yl | H | |
| 42 | n-C₃H₇ | C₂H₅ | isoxazol-3-yl | H | |
| 43 | n-C₃H₇ | C₂H₅ | isoxazol-3-yl | COOCH₃ | |
| 44 | n-C₃H₇ | CH₂CH=CH₂ | isoxazol-3-yl | H | |
| 45 | n-C₃H₇ | CH₂CH=CHCl | isoxazol-3-yl | H | |
| 46 | n-C₃H₇ | C₂H₅ | 5-chlorofur-2-yl | H | viscous oil |
| 47 | n-C₃H₇ | CH₂CH=CH₂ | 5-chlorofur-2-yl | H | 1.5425 (26° C.) |
| 48 | n-C₃H₇ | C₂H₅ | 2-propyl-thiazol-4-yl | H | |
| 49 | n-C₃H₇ | CH₂CH=CH₂ | 2-n-propyl-thiazol-4-yl | H | |
| 50 | n-C₃H₇ | C₂H₅ | 2-phenyl-thiazol-5-yl | H | |
| 51 | n-C₃H₇ | CH₂CH=CH₂ | 2-phenyl-thiazol-5-yl | H | |
| 52 | n-C₃H₇ | CH₂CH=CHCl | 2-phenyl-thiazol-5-yl | H | |
| 53 | n-C₃H₇ | C₂H₅ | 3-phenyl-1,2,4-oxadiazol-5-yl | H | viscous oil |
| 54 | n-C₃H₇ | CH₂CH=CH₂ | 3-phenyl-1,2,4-oxadiazol-5-yl | H | viscous oil |
| 55 | n-C₃H₇ | C₂H₅ | 3-methyl-4-phenyl-1,2,3-triazol-5-yl | H | 1.5620 (25° C.) |
| 56 | n-C₃H₇ | CH₂CH=CH₂ | 3-methyl-4-phenyl-1,2,3-triazol-5-yl | H | 1.5722 (25° C.) |
| 57 | n-C₃H₇ | n-C₃H₇ | 3-methyl-4-phenyl-1,2,3-triazol-5-yl | H | |
| 58 | n-C₃H₇ | CH₂CCl=CH₂ | 3-methyl-4-phenyl-1,2,3-triazol-5-yl | H | |
| 59 | n-C₃H₇ | CH₂CH=CHCl | 3-methyl-4-phenyl-1,2,3-triazol-5-yl | H | |
| 60 | n-C₃H₇ | C₂H₅ | 2-(4-methoxyphenyl)-thiazol-5-yl | H | 97 |
| 61 | n-C₃H₇ | CH₂CH=CH₂ | 2-(4-methoxyphenyl)-thiazol-5-yl | H | 98 |
| 62 | n-C₃H₇ | C₂H₅ | 3-t-butyl-1,2,4-oxadiazol-5-yl | H | |
| 63 | n-C₃H₇ | CH₂CH=CH₂ | 3-t-butyl-1,2,4-oxadiazol-5-yl | H | |
| 64 | n-C₃H₇ | C₂H₅ | 2-(4-methoxypehnyl)-thiazol-4-yl | H | |
| 65 | n-C₃H₇ | CH₂CH=CH₂ | 2-(4-methoxyphenyl)-thiazol-4-yl | H | |
| 66 | n-C₃H₇ | CH₂CH=CHCl | 2-(4-methoxyphenyl)-thiazol-4-yl | H | |
| 67 | n-C₃H₇ | C₂H₅ | 5-methyl-fur-2-yl | COOCH₃ | 1.5249 (22° C.) |
| 68 | n-C₃H₇ | CH₂CH=CH₂ | 5-methyl-fur-2-yl | COOCH₃ | 1.5282 (22° C.) |
| 69 | n-C₃H₇ | C₂H₅ | 5-methyl-fur-2-yl | H | viscous oil |
| 70 | n-C₃H₇ | CH₂CH=CH₂ | 5-methyl-fur-2-yl | H | viscous oil |
| 71 | n-C₃H₇ | C₂H₅ | 2-methyl-thiazol-5-yl | H | |
| 72 | n-C₃H₇ | CH₂CH=CH₂ | 2-methyl-thiazol-5-yl | H | |
| 73 | n-C₃H₇ | C₃H₇ | 2-methyl-thiazol-5-yl | H | |
| 74 | n-C₃H₇ | C₂H₅ | 5-methyl-thiazol-2-yl | H | |
| 75 | n-C₃H₇ | CH₂CH=CH₂ | 5-methyl-thiazol-2-yl | H | |
| 76 | n-C₃H₇ | C₂H₅ | 3-methyl-isoxazol-5-yl | H | 41–44 |
| 77 | n-C₃H₇ | CH₂CH=CH₂ | 3-methyl-isoxzaol-5-yl | H | 72–74 |
| 78 | n-C₃H₇ | C₂H₅ | 3-phenyl-isoxazol-5-yl | COOCH₃ | viscous oil |
| 79 | n-C₃H₇ | CH₂CH=CH₂ | 3-phenyl-isoxazol-5-yl | COOCH₃ | viscous oil |
| 80 | n-C₃H₇ | C₂H₅ | 3-phenyl-isoxazol-5-yl | H | 93–97 |
| 81 | n-C₃H₇ | CH₂CH=CH₂ | 3-phenyl-isoxazol-5-yl | H | 71–73 |
| 82 | n-C₃H₇ | CH₂CH=CHCl | 3-phenyl-isoxazol-5-yl | H | |
| 83 | n-C₃H₇ | C₂H₅ | 5-phenyl-thiozol-2-yl | H | |
| 84 | n-C₃H₇ | CH₂CH=CH₂ | 5-phenyl-thiazol-2-yl | H | |
| 85 | n-C₃H₇ | C₂H₅ | 5-t-butyl-thiazol-2-yl | H | |
| 86 | n-C₃H₇ | CH₂CH=CH₂ | 5-t-butyl-thiazol-2-yl | H | |
| 87 | n-C₃H₇ | C₂H₅ | 2-dimethylamino-thiazol-5-yl | COOCH₃ | 1.5600 (26° C.) |
| 88 | n-C₃H₇ | CH₂CH=CH₂ | 2-dimethylamino-thiazol-5-yl | COOCH₃ | 72–75 |
| 89 | n-C₃H₇ | C₂H₅ | 2-dimethylamino-thiazol-5-yl | H | 78 |
| 90 | n-C₃H₇ | CH₂CH=CH₂ | 2-dimethylamino-thiazol-5-yl | H | 63 |

-continued

| Compound no. | R¹ | R² | X | Z | M.p. [°C.]/n_D |
|---|---|---|---|---|---|
| 91 | n-C₃H₇ | CH₂CH=CHCl | 2-dimethylamino-thiazol-5-yl | H | |
| 92 | C₂H₅ | C₂H₅ | 5-chlorofur-2-yl | COOCH₃ | 1.5331 (22° C.) |
| 93 | n-C₃H₇ | CH₂CH=CH₂ | 5-chlorofur-2-yl | COOCH₃ | 1.5375 (22° C.) |
| 94 | C₂H₅ | C₂H₅ | 5-chlorofur-2-yl | H | viscous oil |
| 95 | C₂H₅ | CH₂CH=CH₂ | 5-chlorofur-2-yl | H | 1.5479 |
| 96 | n-C₃H₇ | C₂H₅ | 2-diethylamino-oxazol-5-yl | H | |
| 97 | n-C₃H₇ | CH₂CH=CH₂ | 2-diethylamino-oxazol-5-yl | H | |
| 98 | n-C₃H₇ | C₂H₅ | thien-3-yl | H | 45–47 |
| 99 | n-C₃H₇ | CH₂CH=CH₂ | thien-3-yl | H | 34–36 |
| 100 | n-C₃H₇ | C₂H₅ | fur-3-yl | H | 55–58 |
| 101 | n-C₃H₇ | CH₂CH=CH₂ | fur-3-yl | H | 1.540 (23° C.) |
| 102 | n-C₃H₇ | CH₂CH=CH₂ | 3-methyl-isoxazol-5-yl | COOCH₃ | |
| 103 | n-C₃H₇ | C₂H₅ | 3-methyl-isoxazol-5-yl | COOCH₃ | |
| 104 | n-C₃H₇ | C₂H₅ | 3-methyl-isoxazol-5-yl | H | 78–80 |
| 105 | n-C₃H₇ | CH₂CH=CH₂ | 3-methyl-isoxazol-5-yl | H | 72–74 |
| 106 | n-C₃H₇ | cis-CH₂CH=CHCl | 3-methyl-isoxazol-5-yl | H | 63–65 |
| 107 | n-C₃H₇ | trans-CH₂CH=CHCl | 3-methyl-isoxazol-5-yl | H | 96–98 |
| 108 | n-C₃H₇ | CH₂CH=CHCl | 3-methyl-isoxazol-5-yl | H | 83–85 |
| 109 | n-C₃H₇ | C₂H₅ | 1-(4-methyl-phenyl)-pyrrol-3-yl | H | |
| 110 | n-C₃H₇ | C₂H₅ | 1-(4-methyl-phenyl)-pyrrol-3-yl | COOCH₃ | |
| 111 | n-C₃H₇ | CH₂CH=CH₂ | 1-(4-methyl-phenyl)-pyrrol-3-yl | H | |
| 112 | n-C₃H₇ | CH₂CH=CHCl | 1-(4-methyl-phenyl)-pyrrol-3-yl | H | |
| 113 | n-C₃H₇ | C₂H₅ | isothiazol-5-yl | H | |
| 114 | n-C₃H₇ | CH₂CH=CH₂ | isothiazol-5-yl | H | |
| 115 | n-C₃H₇ | CH₂CH=CH₂ | 4-methyl-isothiazol-5-yl | H | |
| 116 | n-C₃H₇ | C₂H₅ | 4-methyl-isothiazol-5-yl | H | |
| 117 | n-C₃H₇ | C₂H₅ | 2-(4-chlorophenyl)-thiazol-5-yl | H | |
| 118 | n-C₃H₇ | CH₂CH=CH₂ | 2-(4-chlorophenyl)-thiazol-5-yl | H | |
| 119 | n-C₃H₇ | CH₂CH=CH₂ | 1-(3-trifluoromethyl-phenyl)-pyrrol-3-yl | H | |
| 120 | n-C₃H₇ | C₂H₅ | 1-(3-trifluoromethyl-phenyl)-pyrrol-3-yl | H | |
| 121 | n-C₃H₇ | C₂H₅ | 1-(3,4-dichlorophenyl)-pyrrol-3-yl | H | |
| 122 | n-C₃H₇ | CH₂CH=CH₂ | 1-(3,4-dichlorophenyl)-pyrrol-3-yl | H | |
| 123 | n-C₃H₇ | CH₂—CH=CH₂ | 2-phenyl-thiazol-4-yl | H | 106 |
| 124 | n-C₃H₇ | C₂H₅ | 2-phenyl-thiazol-4-yl | H | 91 |
| 125 | n-C₃H₇ | CH₂—CH=CH₂ | 2-(4-chlorophenyl)-thiazol-5-yl | H | viscous oil |
| 126 | n-C₃H₇ | C₂H₅ | 2-(4-chlorophenyl)-thiazol-5-yl | H | viscous oil |
| 127 | n-C₃H₇ | CH₂—CH=CH₂ | 4-methyl-isothiazol-5-yl | H | 1.563 (22° C.) |
| 128 | n-C₃H₇ | C₂H₅ | 4-methyl-isothiazol-5-yl | H | 1.560 (22° C.) |
| 129 | n-C₃H₇ | CH₂—CH=CH₂ | isothiazol-4-yl | H | 51–55 |
| 130 | n-C₃H₇ | C₂H₅ | isothiazol-4-yl | H | 78–81 |
| 131 | n-C₃H₇ | CH₂—CH=CH₂ (trans) | fur-3-yl | H | 54–57 |
| 132 | n-C₃H₇ | C₂H₅ | 2,5-dimethylthien-3-yl | H | viscous oil |
| 133 | n-C₃H₇ | CH₂—CH=CH₂ | 3-methylisoxazol-5-yl | COOCH₃ | 93–95 |
| 134 | n-C₃H₇ | C₂H₅ | 3-methylisoxazol-5-yl | COOCH₃ | 130–131 |
| 135 | n-C₃H₇ | CH₂—CH=CHCl (cis) | 3-methylisoxazol-5-yl | H | 63–65 |
| 136 | n-C₃H₇ | CH₂—CH=CHCl (trans) | 3-methylisoxazol-5-yl | H | 96–98 |
| 137 | n-C₃H₇ | C₂H₅ | 4-methyl-1,2,3-thiadiazol-5-yl | COOCH₃ | viscous oil |
| 138 | n-C₃H₇ | C₂H₅ | 1-(4-methylphenyl)-pyrrol-3-yl | H | 50–53 |
| 139 | n-C₃H₇ | CH₂—CH=CH₂ | 1-(4-methylphenyl)-pyrrol-3-yl | H | viscous oil |
| 140 | n-C₃H₇ | CH₂—CH=CHCl | 1-(4-methylphenyl)-pyrrol-3-yl | H | viscous oil |
| 141 | n-C₃H₇ | C₂H₅ | 1-(4-methylphenyl)-pyrrol-3-yl | COOCH₃ | viscous oil |
| 142 | n-C₃H₇ | CH₂—CH=CH₂ | 1-(3-trifluoromethylphenyl)-pyrrol-3-yl | H | 50–51 |
| 143 | n-C₃H₇ | C₂H₅ | 1-(3-trifluoromethylphenyl)-pyrrol-3-yl | H | 1.562 (22° C.) |
| 144 | n-C₃H₇ | C₂H₅ | 1-(3,4-dichlorophenyl)-pyrrol-3-yl | H | 1.605 (22° C.) |
| 145 | n-C₃H₇ | CH₂—CH=CH₂ | 1-(3,4-dichlorophenyl)-pyrrol-3-yl | H | viscous oil |
| 146 | n-C₃H₇ | C₂H₅ | N-methyl-imidazol-5-yl | H | |
| 147 | n-C₃H₇ | CH₂—CH=CH₂ | N-methyl-imidazol-5-yl | H | |
| 148 | n-C₃H₇ | CH₂—CH=CHCl (trans) | N-methyl-imidazol-5-yl | H | |
| 149 | C₂H₅ | C₂H₅ | N-methyl-imidazol-5-yl | H | |
| 150 | C₂H₅ | CH₂—CH=CH₂ | N-methyl-imidazol-5-yl | H | |
| 151 | C₂H₅ | CH₂—CH=CHCl (trans) | N-methyl-imidazol-5-yl | H | |
| 152 | n-C₃H₇ | C₂H₅ | 2,3-dimethylimidazol-5-yl | H | |
| 153 | n-C₃H₇ | CH₂—CH=CH₂ | 2,3-dimethylimidazol-5-yl | H | |
| 154 | n-C₃H₇ | CH₂—CH=CHCl (trans) | 2,3-dimethylimidazol-5-yl | H | |
| 155 | C₂H₅ | C₂H₅ | 2,3-dimethylimidazol-5-yl | H | |
| 156 | C₂H₅ | CH₂—CH=CH₂ | 2,3-dimethylimidazol-5-yl | H | |
| 157 | C₂H₅ | CH₂—CH=CH₂Cl (trans) | 2,3-dimethylimidazol-5-yl | H | |
| 158 | n-C₃H₇ | C₂H₅ | N-methylimidazol-2-yl | H | |
| 159 | n-C₃H₇ | CH₂—CH=CH₂ | N-methylimidazol-2-yl | H | |

-continued

| Compound no. | R¹ | R² | X | Z | M.p. [°C.]/$n_D$ |
|---|---|---|---|---|---|
| 160 | n-C₃H₇ | CH₂CH=CHCl (trans) | N-methylimidazol-2-yl | H | |
| 161 | C₂H₅ | C₂H₅ | N-methylimidazol-2-yl | H | |
| 162 | C₂H₅ | CH₂—CH=CH₂ | N-methylimidazol-2-yl | H | |
| 163 | C₂H₅ | CH₂—CH=CHCl (trans) | N-methylimidazol-2-yl | H | |
| 164 | n-C₃H₇ | C₂H₅ | 2-methyl-1,3,4-oxadiazol-5-yl | H | |
| 165 | n-C₃H₇ | CH₂—CH=CH₂ | 2-methyl-1,3,4-oxadiazol-5-yl | H | |
| 167 | n-C₃H₇ | CH₂—CH=CHCl (trans) | 2-methyl-1,3,4-oxadiazol-5-yl | H | |
| 168 | C₂H₅ | C₂H₅ | 2-methyl-1,3,4-oxadiazol-5-yl | H | |
| 169 | C₂H₅ | CH₂—CH=CH₂ | 2-methyl-1,3,4-oxadiazol-5-yl | H | |
| 170 | C₂H₅ | CH₂—CH=CHCl (trans) | 2-methyl-1,3,4-oxadiazol-5-yl | H | |
| 171 | n-C₃H₇ | C₂H₅ | 3-methyl-1,2,5-oxadiazol-4-yl | H | |
| 172 | n-C₃H₇ | CH₂—CH=CH₂ | 3-methyl-1,2,5-oxadiazol-4-yl | H | |
| 173 | n-C₃H₇ | CH₂—CH=CHCl (trans) | 3-methyl-1,2,5-oxadiazol-4-yl | H | |
| 174 | C₂H₅ | C₂H₅ | 3-methyl-1,2,5-oxadiazol-4-yl | H | |
| 175 | C₂H₅ | CH₂—CH=CH₂ | 3-methyl-1,2,5-oxadiazol-4-yl | H | |
| 176 | C₂H₅ | CH₂—CH=CHCl (trans) | 3-methyl-1,2,5-oxadiazol-4-yl | H | |
| 177 | n-C₃H₇ | C₂H₅ | 4-methyl-1,2,3-thiadiazol-5-yl | H | |
| 178 | n-C₃H₇ | CH₂—CH=CH₂ | 4-methyl-1,2,3-thiadiazol-5-yl | H | |
| 179 | n-C₃H₇ | CH₂—CH=CHCl (trans) | 4-methyl-1,2,3-thiadiazol-5-yl | H | |
| 180 | C₂H₅ | C₂H₅ | 4-methyl-1,2,3-thiadiazol-5-yl | H | |
| 181 | C₂H₅ | CH₂—CH=CH₂ | 4-methyl-1,2,3-thiadiazol-5-yl | H | |
| 182 | C₂H₅ | CH₂—CH=CHCl | 4-methyl-1,2,3-thiadiazol-5-yl | H | |
| 183 | n-C₃H₇ | C₂H₅ | 1,2,3-thiadiazol-4-yl | H | |
| 184 | n-C₃H₇ | CH₂—CH=CH₂ | 1,2,3-thiadiazol-4-yl | H | |
| 185 | n-C₃H₇ | CH₂—CH=CHCl (trans) | 1,2,3-thiadiazol-4-yl | H | |
| 186 | C₂H₅ | C₂H₅ | 1,2,3-thiadiazol-4-yl | H | |
| 187 | C₂H₅ | CH₂—CH=CH₂ | 1,2,3-thiadiazol-4-yl | H | |
| 188 | C₂H₅ | CH₂—CH=CHCl (trans) | 1,2,3-thiadiazol-4-yl | H | |
| 189 | n-C₃H₇ | C₂H₅ | 3-methyl-1,2,5-thiadiazol-4-yl | H | |
| 190 | n-C₃H₇ | CH₂—CH=CH₂ | 3-methyl-1,2,5-oxadiazol-4-yl | H | |
| 191 | n-C₃H₇ | CH₂—CH=CHCl (trans) | 3-methyl-1,2,5-oxadiazol-4-yl | H | |
| 192 | C₂H₅ | C₂H₅ | 3-methyl-1,2,5-oxadiazol-4-yl | H | |
| 193 | C₂H₅ | CH₂—CH=CH₂ | 3-methyl-1,2,5-oxadiazol-4-yl | H | |
| 194 | C₂H₅ | CH₂—CH=CHCl (trans) | 3-methyl-1,2,5-oxadiazol-4-yl | H | |
| 195 | n-C₃H₇ | C₂H₅ | 4-methyloxazol-5-yl | H | |
| 196 | n-C₃H₇ | CH₂—CH=CH₂ | 4-methyloxazol-5-yl | H | |
| 197 | n-C₃H₇ | CH₂—CH=CHCl (trans) | 4-methyloxazol-5-yl | H | |
| 198 | C₂H₅ | C₂H₅ | 4-methyloxazol-5-yl | H | |
| 199 | C₂H₅ | CH₂—CH=CH₂ | 4-methyloxazol-5-yl | H | |
| 200 | C₂H₅ | CH₂—CH=CHCl (trans) | 4-methyloxazol-5-yl | H | |
| 201 | C₂H₅ | C₂H₅ | fur-3-yl | H | |
| 202 | C₂H₅ | CH₂—CH=CH₂ | fur-3-yl | H | |
| 203 | C₂H₅ | CH₂—CH=CHCl (trans) | fur-3-yl | H | |

The cyclohexenone derivatives of the formula I, and their salts, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 102 is mixed with 10 parts by weight of N-methyl-alpha-pyrrolidone. A mixture is obtained which is suitable for application in the form of very fine drops.

II. 20 parts by weight of compound no. 71 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 72 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 79 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 81 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 78 is intimately mixed with 97 parts by weight of particulate kaolin. A dust is obtained containing 3% by weight of the active ingredient.

VII. 30 parts by weight of compound no. 94 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 95 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.025 to 3 kg/ha, but is preferably from 0.1 to 1 kg/ha.

The action of the cyclohexenone derivatives of the formula I on plant growth is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or supended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.25, 0.5 and 1.0 kg of active ingredient per hectare. No covers were placed on the vessels in this method.

The pots were set up in the greenhouse - species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Alopecurus myosuroides, Avena fatua, Avena sativa, Bromus inermis, Digitaria sanguinalis, Echinochloa crus-galli, Glycine max., Lolium multiflorum, Setaria italica, Sinapis alba, Sorghum halepense, Triticum aestivum, and Zea mays.

Preemergence Application

On preemergence appllication of 3.0 kg/ha, for example compounds nos. 6, 31, 33, 34, 60, 71, 72, 88, 90, 102, 112, 113, 114, 115, 116 and 120 had a very good action on plants from the grasses family. Broadleaved species, e.g., Sinapis alba, were only damaged slightly, if at all.

Postemergence Application

On postemergence application of compounds nos. 71 and 72, unwanted grassy plants were excellently controlled with 0.25 kg/ha. No damage was caused to broadleaved crop plants such as soybeans. Compounds nos. 78, 79, 81 and 103 chosen by way of example selectively combatted unwanted grassy plants in wheat at a rate of 1.0 kg/ha. Compound no. 102, at 0.5 kg/ha, was also effective on grassy weeds without damaging wheat. For example compounds nos. 77, 108 and 109 had an excellent action in combatting injurious grasses in broadleaved crops, e.g., soybeans.

Compounds nos. 34, 94 and 95, at 0.25 kg/ha, combatted wild oats, a grassy weed selected by way of example, and were selective in wheat.

In view of the spectrum of weeds which can be combatted, the tolerance of the active ingredients according to the invention by crop plants, the desired influence on the growth of crop plants, and in view of the numerous application methods possible, the cyclohexenone derivatives of the formula I may be used in a large number of crop plants.

The following may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize (post directed) |

To increase the spectrumm of action and to achieve synergistic effects, the cyclohexenone derivatives of the formula I, and their salts, may be mixed and applied together with numerous representatives of other herbicidal or growth-regulating active ingredient croups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexenone derivatives of different structure, etc.

It may also be useful to apply the compounds of the formula I, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies.

We claim:

1. A cyclohexenone compound of the formula

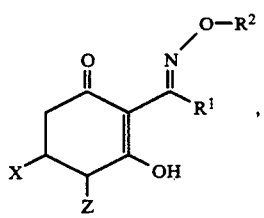

(I)

where $R^1$ is ethyl or n-propyl, $R^2$ is ethyl or —$CH_2$—CH—$CH_2$, X is isoxazol-5-yl substituted by 3-methyl and Z is hydrogen and agriculturally suitable salts thereof.

2. A herbicidal composition containing inert additives and a cyclohexenone compound of the formula I as set forth in claim 1, or a salt thereof.

3. A herbicidal composition as set forth in claim 1, containing from 0.1 to 95 wt % of a cyclohexenone compound of the formula I.

4. A process for combatting weeds, wherein the weeds or the area to be kept free from weeds are treated with a herbicidally effective amount of a cyclohexenone compound of the formula I as set forth in claim 1, or a salt thereof.

5. A process as set forth in claim 1, wherein the amount of cyclohexenone compound of the formula I is from 0.025 to 3 kg/ha.

6. The cyclohexenone compound of the formula I of claim 1, wherein $R^1$ is n—$C_3H_7$, $R^2$ is $CH_2CH=CH_2$, X is 3-methyl-isoxazol-5-yl and Z is H.

7. A cyclohexenone compound of the formula

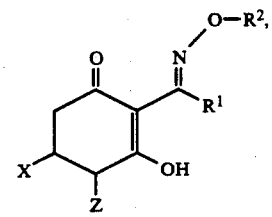

(I)

where $R^1$ is alkyl of 1 to 4 carbon atoms, $R^2$ is alkyl of 1 to 4 carbon atoms, unsubstituted or halogen substituted alkenyl of 3 to 5 carbon atoms or alkynyl of 3 to 5 carbon atoms, X is 3-phenylisoxazol-5-yl and Z is hydrogen, methoxycarbonyl, ethoxycarbonyl, methyl or cyano and agriculturally suitable salts thereof.

8. A cyclohexenone of the formula I as set forth in claim 7, where $R^1$ is n-propyl, $R^2$ is ethyl, and Z is hydrogen.

9. A herbicidal composition containing inert additives and a cyclohexenone compound of the formula I as set forth in claim 7, or a salt thereof.

10. A herbicidal composition as set forth in claim 9, containing from 0.1 to 95 wt % of a cyclohexenone compound of the formula I.

11. A process for combatting weeds, wherein the weeds or the area to be kept free from weeds are treated with a herbicidally effective amount of a cyclohexenone compound of the formula I as set forth in claim 7, or a salt thereof.

12. A process as set forth in claim 11, wherein the amount of cyclohexenone compound of the formula I is from 0.025 to 3 kg/ha.

* * * * *